US012735429B2

(12) United States Patent
Yajima et al.

(10) Patent No.: US 12,735,429 B2
(45) Date of Patent: Sep. 15, 2026

(54) CRYSTAL OF ISOSORBIDE-BIS(TRIMELLITATE ANHYDRIDE) AND METHOD FOR PRODUCING THE SAME

(71) Applicant: HONSHU CHEMICAL INDUSTRY CO., LTD., Tokyo (JP)

(72) Inventors: Kazuhisa Yajima, Wakayama (JP); Ryota Imai, Wakayama (JP)

(73) Assignee: HONSHU CHEMICAL INDUSTRY CO., LTD., Tokyo (JP)

( * ) Notice: Subject to any disclaimer, the term of this patent is extended or adjusted under 35 U.S.C. 154(b) by 289 days.

(21) Appl. No.: 18/712,505

(22) PCT Filed: Nov. 21, 2022

(86) PCT No.: PCT/JP2022/042949
§ 371 (c)(1),
(2) Date: May 22, 2024

(87) PCT Pub. No.: WO2023/112604
PCT Pub. Date: Jun. 22, 2023

(65) Prior Publication Data

US 2025/0034163 A1 Jan. 30, 2025

(30) Foreign Application Priority Data

Dec. 14, 2021 (JP) ................................ 2021-202588

(51) Int. Cl.
*C07D 493/04* (2006.01)

(52) U.S. Cl.
CPC ................................ *C07D 493/04* (2013.01)

(58) Field of Classification Search
CPC .................................................. C07D 493/04
See application file for complete search history.

(56) References Cited

FOREIGN PATENT DOCUMENTS

CN 101648958 A 2/2010

OTHER PUBLICATIONS

International Preliminary Report on Patentability, dated Jun. 13, 2024, for corresponding international application PCT/JP2022/042949 (1 page).
Notification Concerning Transmittal of International Preliminary Report on Patentability, mailed Jun. 27, 2024, for corresponding international application PCT/JP2022/042949 (1 page).
Notification of Transmittal of Translation of the International Preliminary Report on Patentability, mailed Jun. 27, 2024, for corresponding international application PCT/JP2022/042949 (1 page).
Written Opinion of the International Searching Authority, mailed Dec. 27, 2022, for corresponding international application PCT/JP2022/042949 (4 pages).
International Search Report (ISR) mailed Dec. 27, 2022, issued for International application No. PCT/JP2022/042949. (2 pages).

*Primary Examiner* — Bruck Kifle
(74) *Attorney, Agent, or Firm* — Law Office of Katsuhiro Arai

(57) ABSTRACT

An object is to provide a crystal of isosorbide-bis(trimellitate anhydride) having high purity and suitable as a resin raw material. As a solution, provided is a crystal of isosorbide-bis(trimellitate anhydride), particularly, a crystal of isosorbide-bis(trimellitate anhydride) having a melting endothermic peak in a specific range as obtained by differential scanning calorimetry or having a specific peak in a powder X-ray diffraction peak pattern obtained using Cu-Kα radiation.

11 Claims, 2 Drawing Sheets

CRYSTAL OF ISOSORBIDE-BIS(TRIMELLITATE ANHYDRIDE) AND METHOD FOR PRODUCING THE SAME

CROSS-REFERENCE TO RELATED APPLICATIONS

This application is the U.S. National Phase under 35 U.S.C. § 371 of International Application PCT/JP2022/042949, filed Nov. 21, 2022, which claims priority to Japanese Patent Application No. JP2021-202588, filed Dec. 14, 2021. The International Application was published under PCT Article 21(2) in a language other than English.

TECHNICAL FIELD

The present invention relates to a crystal of isosorbide-bis(trimellitate anhydride) and a method for producing the crystal.

BACKGROUND ART

Carboxylic anhydrides, which are compounds widely used in the fields of organic chemistry and polymer chemistry, are a group of compounds useful in a wide variety of fields such as raw materials for pharmaceuticals and agrochemicals, raw materials for resins, and electronic information materials. In particular, carboxylic anhydrides are frequently used in material applications as monomers for polymeric materials such as raw materials for polyimides and polyamides, polyester modifiers, epoxy resin curing agents, etc.

In recent years, bio-based resins obtained using, as such polymeric materials, raw materials derived from biomass resources have been attracting attention as environmentally friendly materials. For example, dianhydrohexitols, which have easily modified hydroxy groups, are increasingly being used because of being expected to have high transparency, high heat resistance, etc. due to their alicyclic structure.

There are few reports on modification of a dianhydrohexitol with an acid anhydride structure, and in the case of modification using trimellitic anhydride, which easily allows modification with an acid anhydride structure, only PTL 1 has made such a report.

CITATION LIST

Patent Literature

PTL 1: Chinese Patent Application Publication No. 101648958

SUMMARY OF INVENTION

Technical Problem

PTL 1 discloses isosorbide-bis(trimellitate anhydride) represented by formula (A) (hereinafter also referred to as compound A) but only shows its production method and NMR data of a substance obtained. When the present inventor conducted an experiment to reproduce the production method, the purity of a substance obtained was low, and a single substance could not be obtained as a crystal.

[Chem. 1]

(A)

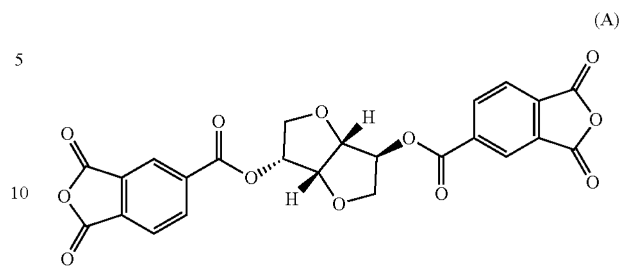

The present invention has been made in view of the foregoing circumstances, and an object thereof is to provide a crystal of compound A having high purity and suitable as a resin raw material.

Solution to Problem

To achieve the above object, the present inventors have conducted intensive studies and found that a crystal of compound A, particularly, a crystal having a melting endothermic peak in a specific range as obtained by differential scanning calorimetry or a crystal having a specific peak in a powder X-ray diffraction peak pattern obtained using Cu-Kα radiation, and a method for producing the crystal, thereby completing the present invention.

The present invention is as follows.

1. A crystal of isosorbide-bis(trimellitate anhydride).
2. The crystal according to 1., wherein a melting endothermic peak obtained by differential scanning calorimetry is in a range of 214° C. to 220° C.
3. The crystal according to 1., having diffraction peaks at diffraction angles 2θ of 17.8°±0.2°, 23.4°±0.2°, 24.8°±0.2°, 27.0°±0.2°, and 30.4°±0.2° in a powder X-ray diffraction peak pattern obtained using Cu-Kα radiation.
4. The crystal according to 1., wherein a melting endothermic peak obtained by differential scanning calorimetry is in a range of 225° C. to 231° C.
5. The crystal according to 1., having diffraction peaks at diffraction angles 2θ of 15.1°±0.2°, 17.9°±0.2°, 19.8°±0.2°, and 29.1°±0.2° in a powder X-ray diffraction peak pattern obtained using Cu-Kα radiation.
6. The crystal according to any one of 1. to 5., wherein a purity of isosorbide-bis(trimellitate anhydride) is 90.0% or more in a gel permeation chromatography measurement.
7. A method for producing the crystal according to 1., including reacting isosorbide and a trimellitic anhydride halide in the presence of a base and an aliphatic nitrile solvent.
8. A method for producing the crystal according to 1., including purifying a solid of isosorbide-bis(trimellitate anhydride) with a solvent including an aromatic hydrocarbon solvent.
9. A method for producing the crystal according to 1., including a step (Step 1) of reacting isosorbide and a trimellitic anhydride halide in the presence of a base and an aliphatic nitrile solvent to obtain a crude crystal and a step (Step 2) of purifying the obtained crude crystal with a solvent.

Advantageous Effects of Invention

The crystal of the present invention makes it possible to handle compound A in a purer and easier-to-handle form than previously possible.

According to the production method of the present invention, compound A can be obtained with high purity and stably as a crystal. In addition, compared with methods known in the art, the crystal can be obtained with a smaller amount of solvent, which can improve industrial production efficiency and also reduce waste, and thus the production method is advantageous for industrial production of compound A and is very useful.

That is, the provision of the crystal of the present invention and the method for producing the crystal is very useful in the industrial use of compound A.

DESCRIPTION OF EMBODIMENTS

<Method of Synthesizing Compound A>

Figure 1:
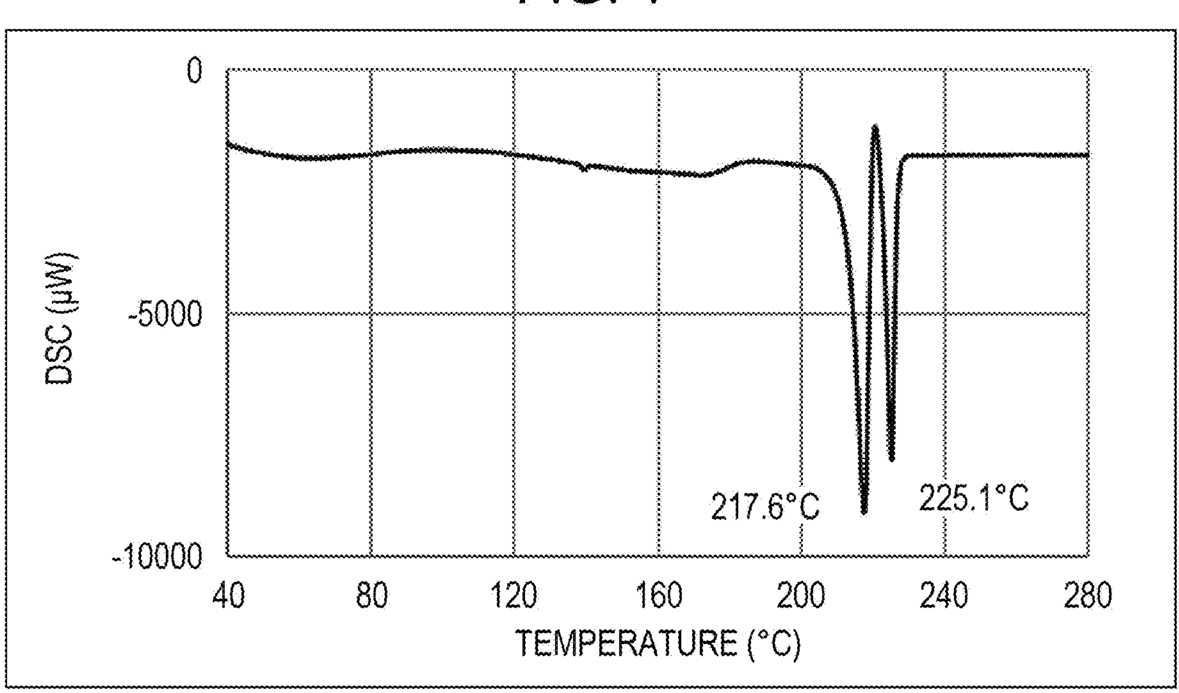
FIG. 1 is a chart showing differential scanning calorimetry data of a crystal obtained in Example 1.

The method of synthesizing compound A according to a crystal of the present invention is not particularly limited, and one example is to react isosorbide and a trimellitic anhydride halide in the presence of a base and a reaction solvent.

[Chem. 2]

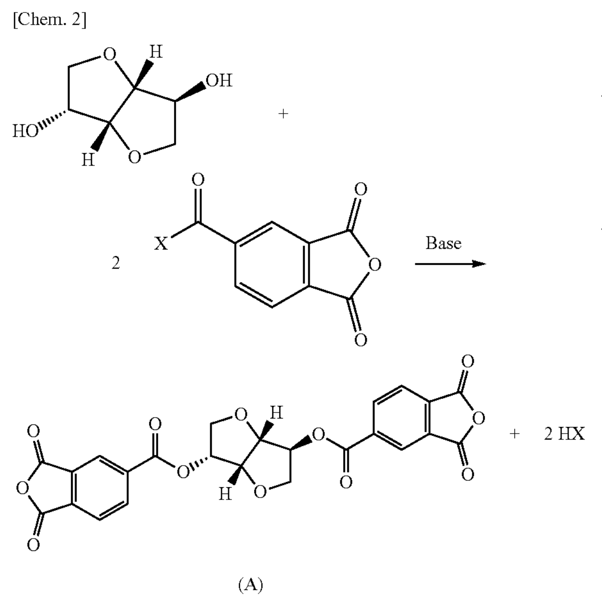

(A)

(In the formula, X represents a halogen atom.)

Examples of trimellitic anhydride halides include trimellitic anhydride chloride, trimellitic anhydride bromide, trimellitic anhydride iodide, and trimellitic anhydride fluoride, and among these trimellitic anhydride halides, trimellitic anhydride chloride is suitable for use because it is inexpensive and easily available.

The amount of trimellitic anhydride halide used is not particularly limited as long as the input molar ratio relative to isosorbide is more than or equal to the theoretical value (2.0), and it is used typically in the range of 2- to 10-fold molar amount, preferably in the range of 2- to 6-fold molar amount, more preferably in the range of 2- to 4-fold molar amount.

Since the reaction between isosorbide and a trimellitic anhydride halide generates a hydrogen halide, the base for capturing the hydrogen halide is used. The base is not particularly limited, and an organic tertiary amine such as pyridine, triethylamine, or N,N-dimethylaniline, an epoxide such as propylene oxide, an inorganic base such as potassium carbonate or sodium hydroxide, or the like can be used. In particular, pyridine is suitable for use from the viewpoint of, for example, separation operation after the reaction, cost, and harmfulness.

The amount of base used is not particularly limited as long as the input molar ratio relative to isosorbide is more than or equal to the theoretical value (2.0), and it is used typically in the range of 2- to 20-fold molar amount, preferably in the range of 2- to 10-fold molar amount, more preferably in the range of 2- to 5-fold molar amount.

The reaction solvent is not particularly limited as long as it does not distill from a reaction vessel at a reaction temperature and is inert to the reaction; examples include aromatic hydrocarbons such as toluene and xylene, aliphatic hydrocarbon solvents such as pentane, hexane, heptane, and cyclohexane, aliphatic ester solvents such as ethyl acetate and n-butyl acetate, lactone solvents such as γ-butyrolactone, aliphatic ketone solvents such as acetone, methyl ethyl ketone, and methyl isobutyl ketone, aliphatic ether solvents such as tetrahydrofuran, dioxane, and methyl-t-butyl ether, and aliphatic nitrile solvents such as acetonitrile and propionitrile.

These reaction solvents may each be used alone, or may be used in combination of two or more as appropriate to adjust polarity. In particular, aliphatic nitrile solvents are preferred.

The amount of reaction solvent used is preferably in the range 1 to 50 times, more preferably in the range of 2 to 20 times, still more preferably in the range of 4 to 15 times the amount of isosorbide on a weight basis.

For reaction conditions, the reaction temperature is preferably in the range of −20° C. to 50° C., more preferably in the range of −10° C. to 25° C. A high reaction temperature is not preferred because the yield decreases due to, for example, hydrolysis of an ester compound formed, and a low reaction temperature is not preferred because the reaction rate slows down. The reaction is typically performed under normal pressure, but depending on the boiling point of an organic solvent used, the reaction may be performed under increased pressure or reduced pressure so that the reaction temperature falls within the above range.

The endpoint of the reaction can be determined by an analysis using liquid chromatography including gel permeation chromatography or gas chromatography. The endpoint of the reaction is preferably defined as the time point at which unreacted isosorbide has disappeared and the increase of compound A of interest is no longer observed. Although the reaction time varies depending on the reaction conditions such as reaction temperature, the reaction is typically completed in about 1 to 30 hours.

(Production Method 1 for Crystal of Present Invention)

The crystal of the present invention can be produced by reacting isosorbide and a trimellitic anhydride halide in the presence of a base and an aliphatic nitrile solvent.

Trimellitic anhydride halides, bases, and aliphatic nitrile solvents as reaction solvents that can be used, the amounts thereof, and the reaction conditions are the same as those in the method of synthesizing compound A described above.

After completion of the reaction, a crystal of compound A of interest is precipitated in a reaction product mixture. Alternatively, the reaction product mixture is cooled, as a result of which a crystal of compound A precipitates.

(Production Method 2 for Crystal of Present Invention)

The crystal of the present invention can be produced by a method including purifying a solid of compound A with a solvent including an aromatic hydrocarbon solvent.

"Purifying" in this Production method 2 means performing a crystallization operation with the solid of compound A dissolved in a solvent or reslurrying the solid of compound A with a solvent.

The solid of compound A can be obtained by subjecting the reaction product mixture of compound A obtained by the synthesis method described above to, for example, solvent distillation, dropwise addition into a poor solvent, column purification, or execution of Production method 1 for the crystal described above. This solid may be amorphous or crystalline. By purifying the solid of compound A by this Production method 2, the purity can be further increased, and in some cases, a crystal having a chemical structure different from that of the crystal before purification can be obtained.

Examples of the aromatic hydrocarbon solvent for use include toluene and xylene. The amount of the aromatic hydrocarbon solvent for use is preferably in the range of 0.5 to 20 times, more preferably in the range of 1 to 10 times, still more preferably in the range of 2 to 6 times the amount of the solid of compound A on a weight basis.

As a solvent for use, a solvent other than aromatic hydrocarbon solvents may be used in combination. Examples of such a solvent include aliphatic hydrocarbon solvents such as pentane, hexane, heptane, and cyclohexane, aliphatic ester solvents such as ethyl acetate and n-butyl acetate, lactone solvents such as γ-butyrolactone, aliphatic ketone solvents such as acetone, methyl ethyl ketone, and methyl isobutyl ketone, aliphatic ether solvents such as tetrahydrofuran, dioxane, and methyl-t-butyl ether, aliphatic nitrile solvents such as acetonitrile and propionitrile, and water. In particular, aliphatic nitrile solvents are preferred. The amount of such a solvent used is preferably 0.1 to 4 times, more preferably 0.1 to 3 times, still more preferably 0.1 to 2 times, particularly preferably 0.1 to 1.5 times the amount of the aromatic hydrocarbon solvent for use on a weight basis.

In this Production method 2, an acid anhydride such as acetic anhydride may be used so that the acid anhydride moiety of compound A, when partially or completely hydrolyzed due to moisture, for example, in the air during handling, undergoes dehydration condensation to return to the acid anhydride.

When a crystallization operation is performed with the solid of compound A dissolved in a solvent, an operation in which the solid of compound A is added to a solvent used for purification and heated to be in the form of a solution, and then cooled is performed.

When the solid of compound A is reslurried with a solvent, an operation in which the solid of compound A is added to a solvent used for purification and heated to be in the form of a slurry, and then cooled is performed.

The addition and heating may be carried out in any order.

Purification by reslurrying is preferred because it does not require a seed crystal and can provide a high-purity crystal of compound A.

The heating is performed to a temperature in the range of 40° C. to 100° C., more preferably in the range of 60° C. to 85° C.

The cooling rate is preferably in the range of 1° C. to 40° C. per hour, more preferably in the range of 2° C. to 30° C. per hour, still more preferably in the range of 5° C. to 20° C. per hour.

The temperature range after cooling is in the range of 0° C. to 40° C., more preferably in the range of 20° C. to 30° C.

(Production Method 3 for Crystal of Present Invention)

The crystal of the present invention can be produced by a method including a step (Step 1) of reacting isosorbide and a trimellitic anhydride halide in the presence of a base and an aliphatic nitrile solvent to obtain a crude crystal and a step (Step 2) of purifying the obtained crude crystal with a solvent.

In Step 1, trimellitic anhydride halides, bases, and aliphatic nitrile solvents as reaction solvents that can be used, the amounts thereof, and the reaction conditions are the same as those in the method of synthesizing compound A described above.

After completion of the reaction, a crude crystal of compound A precipitates in a reaction product mixture. Alternatively, the reaction product mixture is cooled, as a result of which a crude crystal of compound A precipitates.

Step 2 is a step of purifying the crude crystal obtained in Step 1 with a solvent. "Purifying" in Step 2 means performing a crystallization operation with the crude crystal dissolved in a solvent or reslurrying the crude crystal with a solvent.

Examples of solvents for use in Step 2 include aromatic hydrocarbon solvents such as toluene and xylene, aliphatic hydrocarbon solvents such as pentane, hexane, heptane, and cyclohexane, aliphatic ester solvents such as ethyl acetate and n-butyl acetate, lactone solvents such as γ-butyrolactone, aliphatic ketone solvents such as acetone, methyl ethyl ketone, and methyl isobutyl ketone, aliphatic ether solvents such as tetrahydrofuran, dioxane, and methyl-t-butyl ether, aliphatic nitrile solvents such as acetonitrile and propionitrile, and water.

These solvents may each be used alone, or may be used in combination of two or more as appropriate to adjust polarity. In particular, aliphatic nitrile solvents and aromatic hydrocarbon solvents are preferred.

The amount of the solvent used in Step 2 is preferably in the range of 0.5 to 20 times, more preferably in the range of 1 to 10 times, still more preferably in the range of 2 to 6 times the amount of the crude crystal of compound A obtained in Step 1 on a weight basis.

In Step 2, an acid anhydride such as acetic anhydride may be used so that the acid anhydride moiety of compound A, when partially or completely hydrolyzed due to moisture, for example, in the air during handling, undergoes dehydration condensation to return to the acid anhydride.

When a crystallization operation is performed with the crude crystal of compound A dissolved in a solvent, an operation in which the crude crystal of compound A is added to a solvent used for purification and heated to be in the form of a solution, and then cooled is performed.

When the crude crystal of compound A is reslurried with a solvent, an operation in which the crude crystal of compound A is added to a solvent used for purification and heated to be in the form of a slurry, and then cooled is performed.

The addition and heating may be carried out in any order.

In Step 2, purification by reslurrying is preferred because it does not require a seed crystal and can provide a high-purity crystal of compound A.

The heating is performed to a temperature in the range of 40° C. to 100° C., more preferably in the range of 60° C. to 85° C.

The cooling rate is preferably in the range of 1° C. to 40° C. per hour, more preferably in the range of 2° C. to 30° C. per hour, still more preferably in the range of 5° C. to 20° C. per hour.

The temperature after cooling is in the range of 0° C. to 40° C., more preferably in the range of 20° C. to 30° C.

The isolation of the crystal obtained by the above-described method may be performed in accordance with a conventional method; for example, the crystal can be isolated by centrifugal filtration or other means.

Preferably, the crystal is further washed with a solvent. Examples of solvents used here include aromatic hydrocarbon solvents, aliphatic hydrocarbon solvents, aliphatic ester solvents, aliphatic ketone solvents, aliphatic ether solvents, aliphatic nitrile solvents, and water. Specifically, toluene, xylene, pentane, hexane, heptane, cyclohexane, ethyl acetate, n-butyl acetate, γ-butyrolactone, acetone, methyl ethyl ketone, methyl isobutyl ketone, tetrahydrofuran, dioxane, methyl-t-butyl ether, acetonitrile, and propionitrile are preferred, among which toluene, γ-butyrolactone, acetone, methyl ethyl ketone, tetrahydrofuran, and acetonitrile are more preferred, among which acetonitrile is particularly preferred.

The amount of solvent used is in the range 0.5 to 10 times, preferably in the range of 0.5 to 6 times, particularly preferably in the range of 1 to 4 times the amount of the crystal obtained on a weight basis.

By drying the crystal obtained, the solvent used can be removed, and the acid anhydride moiety of compound A, when hydrolyzed during handling, can be allowed to undergo dehydration condensation to return to the acid anhydride. The drying operation can be performed at a temperature preferably in the range of 30° C. to 100° C., more preferably in the range of 40° C. to 80° C. The drying may be performed under normal pressure or reduced pressure, but in the case of industrial practice, it is preferably performed under reduced pressure of about 10 kPa because the solvent used can be removed more efficiently.

The crystal of compound A thus obtained, when used as a polyimide monomer for polymerization, promises to improve reactivity because of its high purity, and is also expected to be excellent in handleability.

<Crystal of Present Invention>

The present invention is a crystal of isosorbide-bis(trimellitate anhydride).

The crystal of the present invention includes at least two kinds of crystals, a crystal A and a crystal B.

The crystal A of the present invention is a crystal having a melting endothermic peak obtained by differential scanning calorimetry in the range of 214° C. to 220° C., preferably in the range of 215° C. to 219° C., more preferably in the range of 216° C. to 219° C., still more preferably in the range of 217° C. to 219° C.

The crystal A of the present invention is also a crystal having diffraction peaks at diffraction angles 2θ of 17.8°±0.2°, 23.4°±0.2°, 24.8°±0.2°, 27.0°±0.2°, and 30.4°±0.2° in a powder X-ray diffraction peak pattern obtained using Cu-Kα radiation.

The crystal B of the present invention is a crystal whose melting endothermic peak obtained by differential scanning calorimetry is in the range of 225° C. to 231° C., preferably in the range of 226° C. to 230° C., more preferably in the range of 227° C. to 230° C., still more preferably in the range of 228° C. to 230° C.

The crystal B of the present invention is also a crystal having diffraction peaks at diffraction angles 2θ of 15.1°±0.2°, 17.9°±0.2°, 19.8°±0.2°, and 29.1°±0.2° in a powder X-ray diffraction peak pattern obtained using Cu-Kα radiation.

In the crystal of the present invention, the purity of compound A is 90.0% or more in a gel permeation chromatography measurement, particularly, compound A is contained in an amount of 90.0 area % or more, preferably 95.0 area % or more, more preferably 97.0 area % or more, still more preferably 98.0 area % or more, relative to the total of all components detected by the gel permeation chromatography measurement.

EXAMPLES

The present invention will now be described specifically with reference to Examples, but it should be noted that the present invention is not limited to these Examples.

Analysis methods are as follows.

<Analysis Methods>

1. Gel Permeation Chromatography (GPC)

Apparatus: HLC-8320GPC (manufactured by Tosoh Corporation)

Detector: differential refractometer (RI)

(Measurement Conditions)

Mobile phase: tetrahydrofuran (containing stabilizer)

Flow rate: 1.0 mL/min

Injection volume: 100 μL

Column temperature: 40° C.

Column: TSKgel guardcolumn HXL-L, one; TSKgel G2000HXL, two; TSKgel G3000HXL, one; TSKgel G4000HXL, one 2. Differential Scanning Calorimetry (DSC)

A crystal was accurately weighed into an aluminum pan and measured using the following differential scanning calorimeter under the following measurement conditions with aluminum oxide as a control.

Apparatus: DSC7020 (manufactured by Hitachi High-Tech Science Corporation)

(Measurement Conditions)

Heating rate: 10° C./min

Measurement temperature range: 30° C. to 300° C.

Measurement atmosphere: open; nitrogen, 50 mL/min

Sample volume: 3 mg±1 mg

3. Powder X-Ray Diffraction (XRD)

A crystal in an amount of 0.1 g was loaded in a sample loading section of a glass test plate and measured using the following powder X-ray diffractometer under the following conditions.

Apparatus: MiniFlex600 (manufactured by Rigaku Corporation)

(Measurement Conditions)

X-ray source: Cu-Kα

Scan axis: 2θ/θ

Mode: continuous

Measurement range: 2θ=5° to 90°

Step: 0.02°

Speed measurement time: 2θ=10°/min

Divergence slit: ¼
Receiving slit: 13.00 mm
Output: 40 kV-15 mA

Example 1

(Crystal of Present Invention: Example of Production Method 1 and Step 1 of Production Method 3)

In a four-necked flask equipped with a thermometer, a stirrer, and a condenser, 59.1 g (0.28 mol) of trimellitic anhydride chloride and 80.0 g of acetonitrile were loaded. While the mixture was dissolved by stirring, the reaction vessel was purged with nitrogen and cooled to 5° C. or lower. Thereafter, a prepared solution in which 20.0 g (0.14 mol) of isosorbide, 100.0 g of acetonitrile, and 32.5 g (0.41 mol) of pyridine were dissolved was added dropwise at a constant rate over 2 hours while maintaining the temperature in the reaction vessel at 5° C. or lower. After completion of the dropwise addition, stirring was performed at 5° C. or lower for 1 hour. Thereafter, the resulting mixture was heated to 25° C. and stirred overnight. The white solid formed was separated by filtration and obtained in an amount of 48.2 g. The white solid obtained was subjected to a GPC measurement, and it was found that compound A accounted for 96.3 area % (purity, 96.3%) relative to the total of all components detected by GPC.

The white solid obtained was subjected to a differential scanning calorimetry analysis, and melting endothermic peaks were observed. This result showed that the white solid obtained was a crystal. A chart showing the data of this differential scanning calorimetry analysis is shown in FIG. 1. The melting endothermic peaks obtained by this differential scanning calorimetry analysis were at 217.6° C. and 225.1° C.

Figure 2:
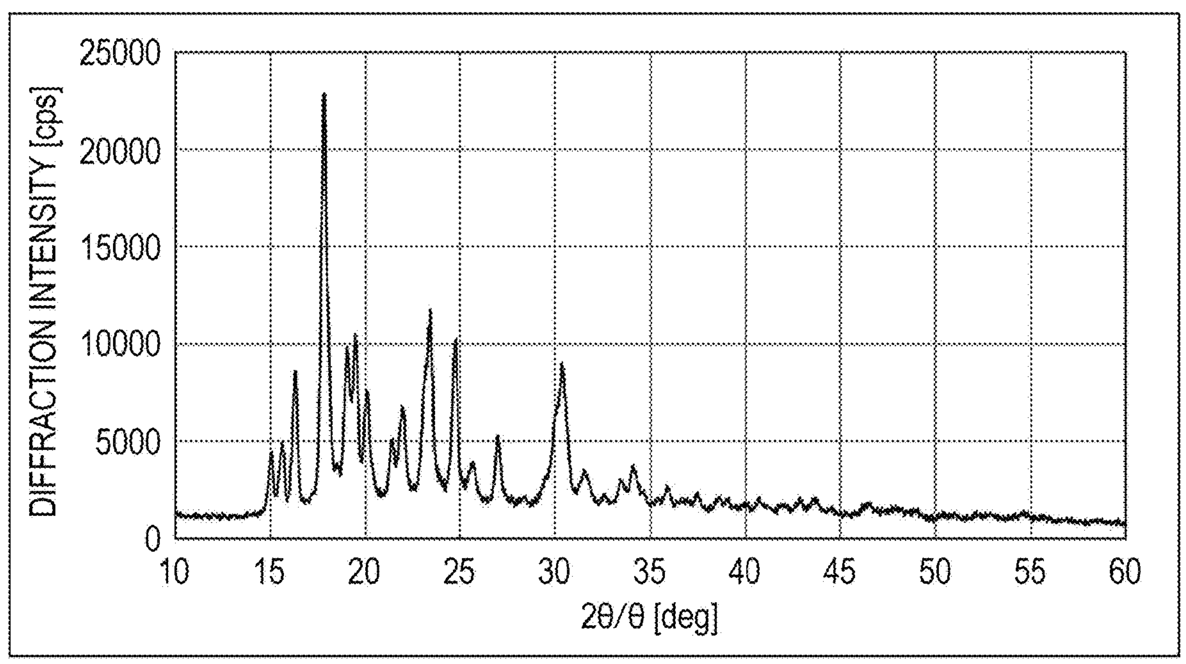
FIG. 2 is a chart showing powder X-ray diffraction data of the crystal obtained in Example 1, the data being obtained using Cu-Kα radiation.

Furthermore, the white solid obtained was subjected to a powder X-ray diffraction measurement using Cu-Kα radiation, and a peak pattern also showed that the white solid obtained was a crystal. A chart showing the data of this powder X-ray diffraction using Cu-Kα radiation is shown in FIG. 2. The diffraction angle 2θ (') of diffraction peaks that appeared and their relative intensity based on the most intense peak are shown in Table 1.

TABLE 1

| 2θ/θ (°) | Relative intensity |
|---|---|
| 15.08 | 0.19 |
| 15.64 | 0.22 |
| 16.34 | 0.36 |
| 17.84 | 1.00 |
| 19.04 | 0.43 |
| 19.46 | 0.46 |
| 20.06 | 0.33 |
| 21.40 | 0.22 |
| 21.90 | 0.30 |
| 23.40 | 0.52 |
| 24.76 | 0.45 |
| 26.96 | 0.23 |
| 30.36 | 0.39 |

Example 2

(Crystal of Present Invention: Example of Production Method 2 and Step 2 of Production Method 3)

The white solid obtained in Example 1 in an amount of 46.0 g was reslurried at 80° C. using 114.8 g of acetonitrile, 92.3 g of toluene, and 2.2 g of acetic anhydride. Thereafter, after cooling to 25° C., the solid was filtered and dried by heating to 80° C. under reduced pressure to obtain 36.7 g of a white solid.

The white solid obtained was subjected to a GPC measurement, and it was found that compound A accounted for 99.0 area % (purity, 99.0%) relative to the total of all components detected by the GPC measurement.

Figure 3:
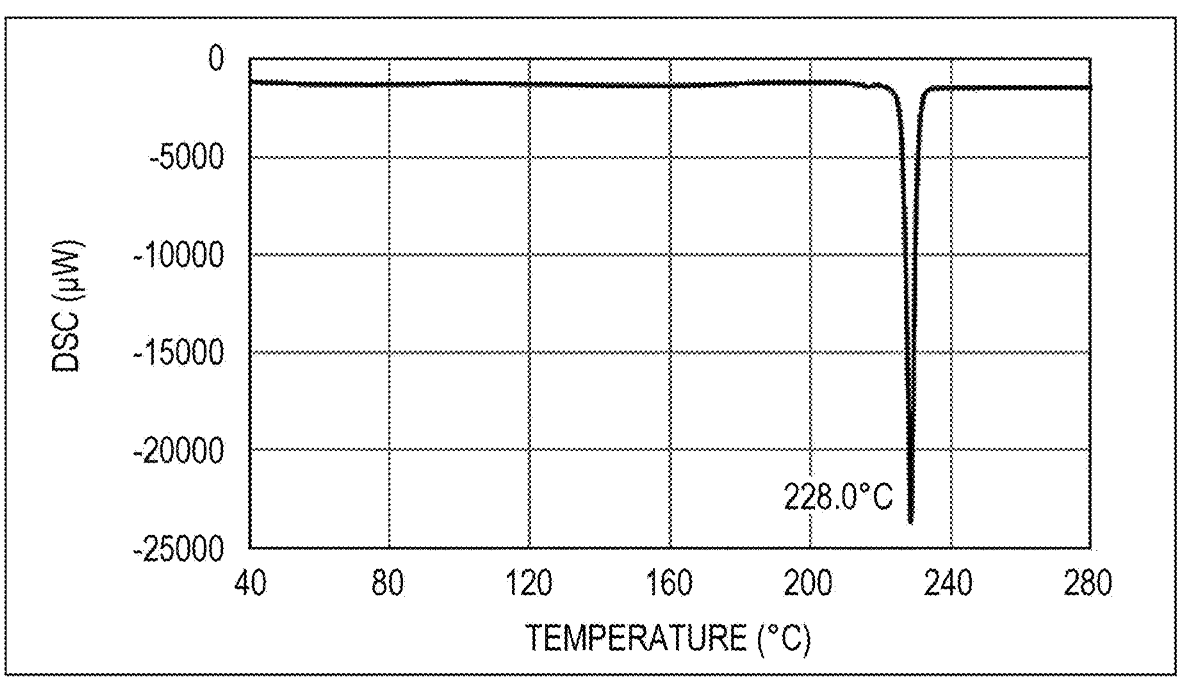
FIG. 3 is a chart showing differential scanning calorimetry data of a crystal obtained in Example 2.

The white solid obtained was subjected to a differential scanning calorimetry analysis, and a melting endothermic peak was observed. This result showed that the white solid obtained was a crystal. A chart showing the data of this differential scanning calorimetry analysis is shown in FIG. 3. The melting endothermic peak obtained by this differential scanning calorimetry analysis was at 228.0° C.

Figure 4:
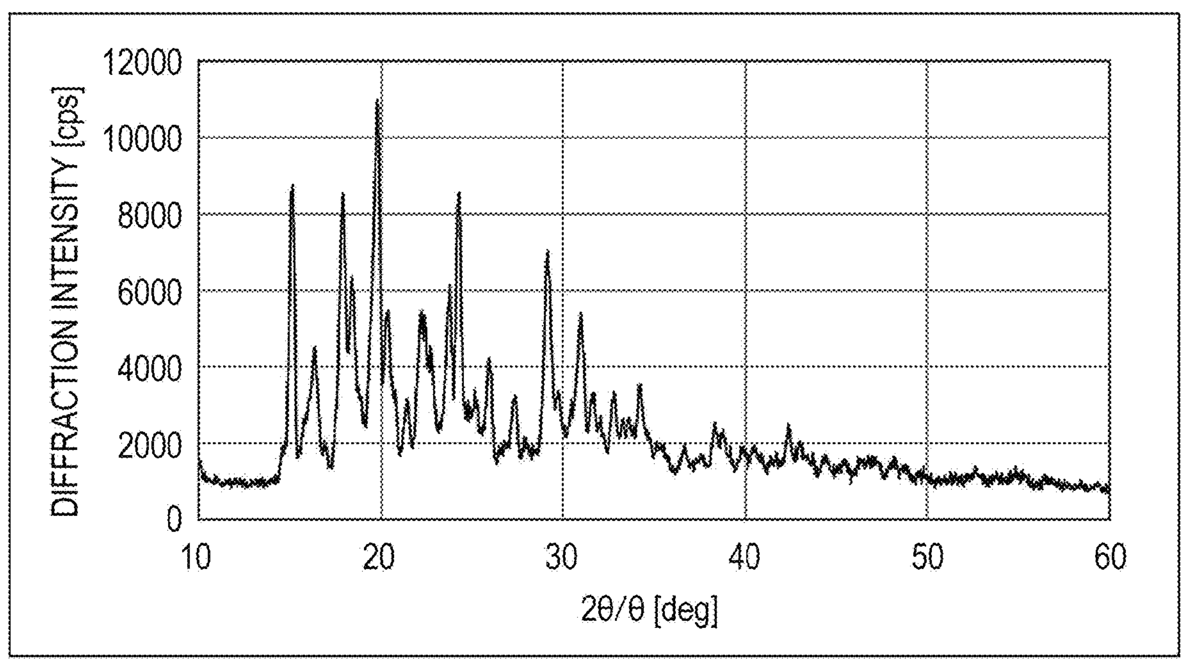
FIG. 4 is a chart showing powder X-ray diffraction data of the crystal obtained in Example 2, the data being obtained using Cu-Kα radiation.

Furthermore, the white solid obtained was subjected to a powder X-ray diffraction measurement using Cu-Kα radiation, and a peak pattern also showed that the white solid obtained was a crystal. A chart showing the data of this powder X-ray diffraction using Cu-Kα radiation is shown in FIG. 4. The diffraction angle 2θ (°) of diffraction peaks that appeared and their relative intensity based on the most intense peak are shown in Table 2.

TABLE 2

| 2θ/θ (°) | Relative intensity |
|---|---|
| 15.14 | 0.80 |
| 16.34 | 0.41 |
| 17.9 | 0.78 |
| 18.4 | 0.58 |
| 19.78 | 1.00 |
| 20.34 | 0.49 |
| 21.4 | 0.29 |
| 22.22 | 0.50 |
| 23.76 | 0.56 |
| 24.28 | 0.78 |
| 27.38 | 0.30 |
| 29.14 | 0.64 |
| 30.98 | 0.49 |
| 34.24 | 0.32 |

Comparative Example 1

In a four-necked flask equipped with a thermometer, a stirrer, and a condenser, 10.0 g (0.07 mol) of isosorbide, 6.0 g of pyridine, and 168.0 g of dehydrated tetrahydrofuran were loaded. While the mixture was dissolved by stirring, the reaction vessel was purged with nitrogen and cooled to 10° C. Thereafter, 33.2 g (0.16 mol) of trimellitic anhydride chloride was added while maintaining the temperature in the reaction vessel at 10° C. After completion of the addition, the resulting mixture was stirred at 10° C. for 24 hours, and the precipitate formed was removed by filtration to obtain a homogeneous yellow solution.

The yellow solution obtained was slowly added dropwise to 34 volumes of petroleum ether, and the solid formed was filtered and dried under reduced pressure at 80° C. to obtain 10.7 g of a white solid.

The white solid obtained was subjected to a GPC measurement, and it was found that compound A accounted for 49.8 area % (purity, 49.8%) relative to the total of all components detected by the GPC measurement.

The white solid obtained was subjected to a differential scanning calorimetry analysis, and no melting endothermic peaks were observed. This result showed that the white solid obtained was not a crystal.

The invention claimed is:

1. A crystal of isosorbide-bis(trimellitate anhydride) having diffraction peaks at diffraction angles 2θ of 17.8°±0.2°, 23.4°±0.2°, 24.8°=0.2°, 27.0°±0.2°, and 30.4°±0.2° in a powder X-ray diffraction peak pattern obtained using Cu-Kα radiation.

2. The crystal according to claim 1, wherein a melting endothermic peak obtained by differential scanning calorimetry is in a range of 214° C. to 220° C.

3. The crystal according to claim 2, wherein a purity of isosorbide-bis(trimellitate anhydride) is 90.0% or more in a gel permeation chromatography measurement.

4. The crystal according to claim 1, wherein a purity of isosorbide-bis(trimellitate anhydride) is 90.0% or more in a gel permeation chromatography measurement.

5. A method for producing the crystal according to claim 1, comprising reacting isosorbide and a trimellitic anhydride halide in the presence of a base and an aliphatic nitrile solvent.

6. A crystal of isosorbide-bis(trimellitate anhydride) having diffraction peaks at diffraction angles 2θ of 15.1°±0.2°, 17.9°±0.2°, 19.8°±0.2°, and 29.1°±0.2° in a powder X-ray diffraction peak pattern obtained using Cu-Kα radiation.

7. The crystal according to claim 5, wherein a melting endothermic peak obtained by differential scanning calorimetry is in a range of 225° C. to 231° C.

8. A method for producing the crystal according to claim 5, comprising purifying a solid of isosorbide-bis(trimellitate anhydride) with a solvent including an aromatic hydrocarbon solvent.

9. A method for producing the crystal according to claim 6, comprising a step (Step 1) of reacting isosorbide and a trimellitic anhydride halide in the presence of a base and an aliphatic nitrile solvent to obtain a crude crystal and a step (Step 2) of purifying the obtained crude crystal with a solvent.

10. The crystal according to claim 6, wherein a purity of isosorbide-bis(trimellitate anhydride) is 90.0% or more in a gel permeation chromatography measurement.

11. A crystal of isosorbide-bis(trimellitate anhydride) having diffraction peaks at diffraction angles 2θ of 15.1°±0.2°, 17.9°±0.2°, 19.8°±0.2°, and 29.1°±0.2° in a powder X-ray diffraction peak pattern obtained using Cu-Kα radiation, wherein a melting endothermic peak obtained by differential scanning calorimetry is in a range of 225° C. to 231° C., and a purity of isosorbide-bis(trimellitate anhydride) is 90.0% or more in a gel permeation chromatography measurement.

* * * * *